United States Patent [19] [11] Patent Number: 4,606,118
Cannon et al. [45] Date of Patent: Aug. 19, 1986

[54] METHOD OF MAKING A DRUG DISPENSING BODY

[75] Inventors: Norbert H. Cannon, St. Paul, Minn.; James E. Graf, Ames, Iowa

[73] Assignee: Medtronic, Inc., Minneapolis, Minn.

[21] Appl. No.: 706,214

[22] Filed: Feb. 27, 1985

[51] Int. Cl.$^4$ ............................................. H01R 43/00
[52] U.S. Cl. ........................................ 29/825; 29/877
[58] Field of Search ................... 29/825, 877; 128/789, 128/785, 786, 419 P; 204/224 R

[56] References Cited

U.S. PATENT DOCUMENTS 4,063,352 12/1977 Bevilacqua ..................... 29/877 X
4,393,584 7/1983 Bare et al. ............................. 29/877
4,506,680 3/1985 Stokes .................................. 128/786

FOREIGN PATENT DOCUMENTS 47013 3/1982 European Pat. Off. ............ 128/786
57450 8/1982 European Pat. Off. ............ 128/785
57451 8/1982 European Pat. Off. ............ 128/785
57877 8/1982 European Pat. Off. ............ 128/785

Primary Examiner—Howard N. Goldberg
Assistant Examiner—Carl J. Arbes
Attorney, Agent, or Firm—Reed A. Duthler; Joseph F. Breimayer; John L. Rooney

[57] ABSTRACT

A body implantable lead for the delivery of stimulation energy to a desired body site including a drug dispenser carried by the lead which retains a drug to be dispensed while allowing the dispensing of that drug at least adjacent the desired body stimulation site. The lead is provided with an electrode having a bore open to a drug storage chamber which contains an absorbent plug. The drug is loaded into the absorbent plug, prior to use, by soaking the electrode in a solution containing the drug.

2 Claims, 1 Drawing Figure

METHOD OF MAKING A DRUG DISPENSING BODY

CROSS REFERENCE TO COMMONLY ASSIGNED U.S. PATENT reference is made to U.S. Pat. No. 4,506,680 Stokes for a Drug Dispensing Body Implantable Lead, filed March 17, 1983 issued March 26, 1985.

BACKGROUND OF THE INVENTION

This invention pertains to electrical stimulation leads in general, and to cardiac pacing leads in particular.

Electrical stimulation of the body for medical purposes is well known in the prior art. An example of a device for this purpose is the well-known cardiac pacemaker. In the pacemaker context, as well as other body stimulation contexts, the stimulation is delivered to the desired body site by an electrode carrying lead.

Interactions between the lead and body can vitiate the desired effects of the stimulation. For example, biologic reactions may encourage fibrosis. In the pacemaking context, fibrosis is believed to be a major factor in the increase in chronic stimulation threshold that is usually experienced. Also, trauma results in inflamation of the tissue to be stimulated. Such inflamation may alter the response of the tissue to the stimulation energy, both acutely and chronically.

Other interactions between the lead and body, while not directly affecting the response of the tissue to the stimulation energy, can result in the occurrence of undesirable events. In some circumstances where electrical body stimulation is indicated, the body portion to be stimulated is irritable. The placement of a lead may compound this irritability. For example, the placement of a pacemaking lead may induce a cardiac arrhythmia. The presence of the lead may also promote thrombus formation.

The interactions noted above have long been recognized and efforts made to ameliorate their consequences. For example, the lead may be configured to reduce mechanical trauma and the response of irritable tissue during lead placement. Materials may be selected for the lead body and electrodes to minimize fibrosis. However, lead configuration must take into account other factors such as the efficiency of the delivery of the stimulation energy, the ease of lead placement, maintenance of the desired electrode position and reliability of the lead over extended periods of time. An accommodation of these interests has resulted in leads whose configuration necessarily results in undesirable interactions between the lead and body.

It is known that thrombus formation may also be countered by the administration of suitable drugs. It is also known that a systemic treatment with steroids results in acute reduction in the stimulation threshold level. In particular, systemic use of glucocorticosteroids has been used to treat chronic exit block, a condition in which the stimulation threshold rises above the output level of the implanted pacemaker. However, long term systemic use of such steroids often produces undesirable side effects.

SUMMARY OF THE INVENTION

The present invention provides a body implantable lead for the delivery of stimulation energy to a desired body site. A drug dispenser carried by the lead includes a member for retaining the drug to be dispensed while allowing a dispensing of that drug at the desired body stimulation site. The drug may be one intended to counter fibrosis, inflamation, or arrhythmias, or any combination thereof, or to accomplish any desirable localized purpose. In a preferred embodiment as a cardiac pacing lead, the drug may be the sodium salt of dexamethasone phosphate, a glucocorticosteroid which, when dispensed by a lead according to the present invention, results in a chronic reduction of pacing and sensing thresholds. Most preferably, the lead carries a tip electrode at its distal end with the drug being dispensed through a porous, sintered elution path within the electrode. In some embodiments, it is desirable to additionally apply the drug to a porous portion of the tip electrode, adjacent the exit point of the elution path.

Because many drugs, including glucocorticosteroids, may lose effectiveness after prolonged periods of storage, or after exposure to excessive heat or light, manufacture of a drug dispensing electrode poses problems not encountered in the manufacture of a typical pacing lead. All manufacturing steps subsequent to insertion of the drug into the lead structure must be carried out at a temperature below the temperature at which the drug looses effectiveness. This factor works against process steps in which the electrode is exposed to high temperatures for a long period of time, and poses severe restraints on the use of welding to connect various electrode structures to one another. A prior steroid eluting lead is described in commonly assigned U.S. Pat. No. 4,506,680 issued to Stokes, reference above. These drug eluting electrodes used a monolithic controlled release device formed by compounding steroid in powder form with medical adhesive. The shelf life of such leads is limited to the shelf life of the drug used which itself may have been compounded before final assembly and sterilization. The shelf life of a typical pacing lead is limited only by the ability of its packaging to retain sterility and can be extended by resterilization.

The present invention allows the drug to be loaded into the pacing electrode as a final manufacturing step, so that shelf life is proportionately extended and correlates with final assembly of the lead rather than with an earlier step of compounding the steroid with medical adhesive. Further, the present invention opens the possibility that the lead may be manufactured and sterilized before the incorporation of a drug which provides two distinct advantages.

First, shelf life of the non-loaded lead is limited only by the ability of the packaging to retain sterility. Second, it allows the physician to perform the final soaking step and therefore allows the physician to select the type and strength of drug to be applied. Because the volume of the drug chamber and the absorbency of the material within the chamber are determinable, accurate dosing is possible by varying the concentration of the soaking solution, and soaking until the absorbent plug is saturated.

This invention, and its advantages, may be more fully understood in conjunction with the following detailed description.

DESCRIPTION OF THE INVENTION

Detailed Description of the Drawings

Figure 1:
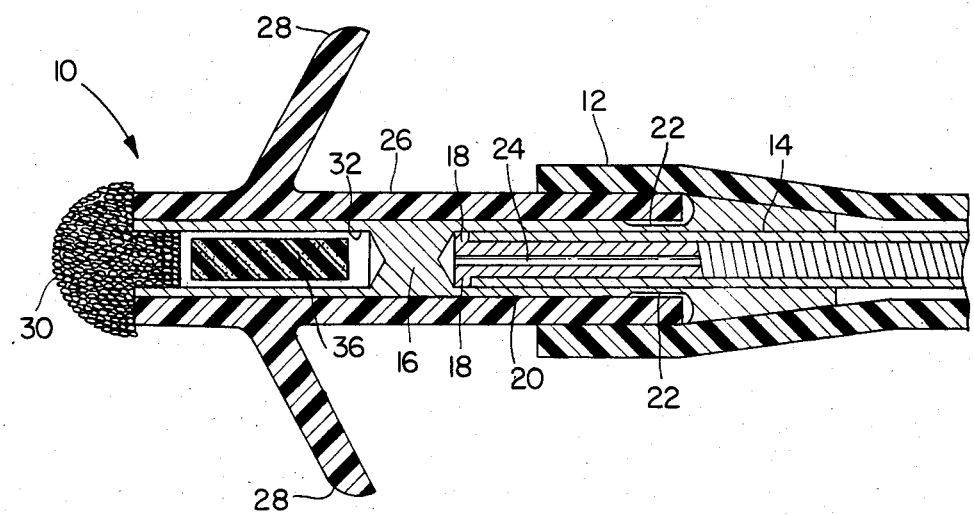
FIG. 1. illustrates a side sectional view of a preferred embodiment of the proximal portion of a pacing lead employing the present invention.

FIG. 1 illustrates a side sectional view of the proximal end of a lead according to the present invention. The proximal end of lead 10 is provided with a porous, sintered electrode 30, which is welded or crimped to an inner electrode member 16. Inner electrode member 16 is provided with a first bore 32, which forms a drug storage chamber, and is provided with a second bore 20, the function of which will be discussed below. Surrounding inner electrode member 16 is insulative sheath 26 which is provided with four tines 28, the function of which is described in U.S. Pat. No. 3,902,501 issued to Citron et al incorporated herein by reference in its entirety. Insulative sheath 26 is preferably fabricated of silicone rubber, polyurethane or other pliant insulative materials.

Plug 36 is fabricated of an absorbent material such as cellulose, natural sponge, or other appropriate fibrous material. In such embodiments, it is desirable that plug 36 be smaller than bore 32, to allow for expansion of the plug as the drug solution is absorbed. Alternatively, plug 36 may be fabricated of an inelastic material, such as porous glass, ceramic, plastic or metal having pores of appropriate size for encouraging absorbance of the drug solution by means of capillary action.

As such, the method of manufacture of the present invention differs from that of the prior art in that the absorbent plug, which serves as a monolithic controlled release device, is first incorporated into the lead and later filled with the desired drug by soaking the electrode. This novel manufacturing method leads to the advantages discussed above.

Prior to use, the electrode 30 is soaked in a solution of the desired drug until plug 36 is fully saturated. This soaking also has the effect of saturating the elution path of electrode 30 and coating electrode 30's outer surface with the drug adjacent the elution path which assists in providing efficient flow of the drug through the elution path.

In operation, upon implant, body fluids enter bore 32 by means of porous, sintered electrode 30. The elution rate of the drug, out of plug 36 and into body fluid via porous electrode 30 may be controlled by varying the porosity of electrode 30 and of plug 32. In a pacing lead, in which the drug is intended to reduce irritability, fibrosis, or other electrode related problems, the fact that the drug is dispensed directly through the electrode is believed to be beneficial.

The proximal portion of inner electrode member 14 serves as the means for attachment of a coiled conductor, and pacing lead body, typical of those in the prior art. Within bore 20 is shown coiled conductor 14, which is maintained in firm electrical contact with inner electrode member 16 by means of internal swaging bore 18 and crimps 22, which tightly clamp coil 14 between inner electrode member 16 and the swaging core. Insulative sheath 12 extends from the distal portion of the lead, to an electrical connector, at the proximal end of the lead. The proximal portion of this pacing lead may be constructed according to the disclosure of U.S. Pat. No. 4,258,725 issued to O'Neill and incorporated herein by reference in its entirety.

Other and further embodiments of the invention are readily apparent from the above description of the invention, and these embodiments are believed to be within the scope of the invention disclosed herein.

What is claimed is:

1. A method of manufacturing a drug eluting electrode, comprising the ordered steps of:
    fabricating an electrode body including a drug chamber open to the exterior of said electrode body;
    inserting an absorbent plug into said drug chamber of said electrode;
    packaging and sterilizing said electrode; and
    after said inserting step and said packaging and sterilizing step, soaking said electrode body in a liquid solution of a desired drug until said absorbent plug is saturated with said drug.

2. A method of manufacturing a drug eluting electrode, comprising the ordered steps of:
    fabricating an electrode body including a drug chamber and having a bore open to said drug chamber and open to the exterior of said electrode and having a porous surface on the exterior of said electrode adjacent said bore;
    inserting an absorbent plug into said drug chamber of said electrode; and
    after said inserting step, soaking said electrode body including said porous surface of said electrode body in a liquid solution of a desired drug until said absorbent plug is saturated with said drug.

* * * * *